United States Patent [19]

Goupil

[11] 4,323,550
[45] Apr. 6, 1982

[54] HALOGENOHYDRATES OF N,N-DISUBSTITUTED DERIVATIVES OF PIPERAZINE HAVING ANTICARIOGENIC PROPERTIES

[76] Inventor: Jean-Jacques Goupil, 30 Ave du President Wilson, Cachan, France, 94230

[21] Appl. No.: 769,588

[22] Filed: Feb. 17, 1977

[30] Foreign Application Priority Data

Feb. 19, 1976 [FR] France .................. 76 04546

[51] Int. Cl.$^3$ .................. A61K 7/18; C07D 295/08
[52] U.S. Cl. .................. 424/52; 544/374; 544/401
[58] Field of Search .................. 260/268 R, 268 H; 424/250; 544/374, 401

[56] References Cited

U.S. PATENT DOCUMENTS 3,124,512 3/1964 Schmid et al. .................. 424/52
3,277,118 10/1966 Schmid et al. .................. 424/52

OTHER PUBLICATIONS

Sharts & Sheppard–Organic Reactions–vol. 21–pp. 201–204; 216–219 (1974) (John Wiley & Sons, Inc., New York).

Elderfield–Heterocyclic Compounds–vol. 1–pp. 23–24 (1950) (John Wiley & Sons, Inc., New York).

Paul et al. J. Med. Chemistry, vol. 16, No. 12, 1391–1394 (1973).

Gardner et al., J. Amer. Chem. Soc., vol. 55, 3823 (1933).

*Primary Examiner*—Anton H. Sutto
*Attorney, Agent, or Firm*—Darby & Darby

[57] ABSTRACT

Halogenohydrates of N,N'-disubstituted derivatives of piperazine of the general formula:

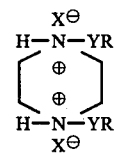

wherein YR is a hydroxylalkyl, polyhydroxyalkyl or epoxyalkyl wherein Y is a hydroxy, polyhydroxy or epoxy group, R is lower alkyl $C_2$-$C_4$, and X is a member selected from the group consisting of fluorine, bromine, chlorine and iodine. The compounds have useful anticariogenic properties.

11 Claims, No Drawings

HALOGENOHYDRATES OF N,N-DISUBSTITUTED DERIVATIVES OF PIPERAZINE HAVING ANTICARIOGENIC PROPERTIES

The present invention has as its object new halogenohydrates of N,N'-disubstituted derivatives of piperazine of the formula:

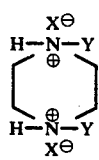

in which Y is a hydroxyalky, polyhydroxyalkyl or epoxyalkyl group, and X is fluorine, chlorine, bromine or iodine.

The invention also has as its object the application of the anticarioigenic properties of the new compounds.

The preparation of the halogenohydric acids of the corresponding bases, namely the N,N'-di(hydroxyalkyl) piperazines, N,N'-di(polyhydroxyalkyl) piperazines and N,N'-di(epoxy-alkyl) piperazines.

The latter result from the condensation of a hydroxyalkyl, polyhydroxyalkyl or epoxy-alkyl halide with anhydrous piperazine in the presence of proton acceptor catalysts ($CO_3Na_2$, $CO_3K_2$...) in a suitable reaction medium, constituted by a solvent of high dielectric constant, such as acetone or dimethyl formamide, permitting gentle, selective alkylations, with good yields.

For example, the preparation of N,N'-di(hydroxyethyl) piperazine:

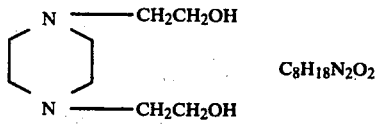

occurs in the following manner:

The different reagents—piperazine, dimethyl formamide and potassium carbonate (calcined)—are introduced into a three-necked flask with mechanical agitator and provided with a reflux condenser.

Under vigorous agitation, beta-chloro-ethanol is added drop by drop over a period of about 10 to 15 minutes.

The agitation is maintained and the reaction mass is heated to about 80° C. for 2 hours. The reaction mass is left to stand overnight.

Next day cool to about 60° C., dry to eliminate $CO_3K_2$ and (other mineral impurities), wash the precipitate 2 or 3 times with anhydrous chloroform. Under adequate vacuum drive out a part of excess dimethyl formamide and all the wash chloroform.

Leave in a cold place, dry the product obtained, wash it with ether and crystallize it in methanol. One obtains fine colorless crystals of N,N'-dihydroxyethylpiperazine having a melting point of 137° C.

Likewise N,N'-di(dihydroxy-propyl) piperazine of the formula:

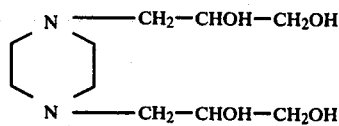

is obtained by the same process and occurs in the form of fine colorless crystals of melting point 188° C. Lastly, N,N'-di(epoxy-propyl) piperazine is prepared by the same process and has the formula:

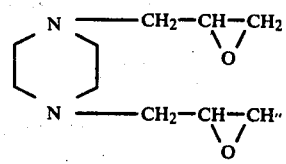

The preparation of the difluorohydrates of the above bases occurs by cold dissolution of one mole of the chosen base in two moles of fluorhydric acid in aqueous solution of 20, 30 or 40%. The excess cold water is then eliminated with a desiccator (potassium or phosphoric anhydride), then crystallizing in absolute ethanol.

Fine colorless crystals are obtained.

DIFLUOROHYDRATE OF N,N'-DI(HYDROXY-ETHYL) PIPERAZINE

Fine colorless, very hygroscopic crystals melting point equals 54°–56° C.

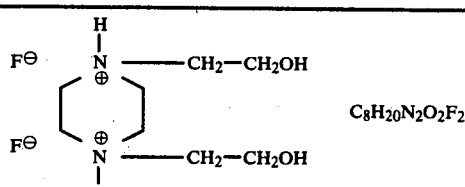

| Percentage composition | Calculated | Mol. wt. = 214 Found |
|---|---|---|
| Carbon % | 44.90 | 44.3–44.6 |
| Hydrogen % | 9.42 | 9.79–10 |
| Nitrogen % | 13.09 | 12.95 |
| Fluorine % | 17.76 | 17.58–17.96 |

The test by NMR spectrometry shows that fluorohydrate has been formed.

DIFLUOROHYDRATE OF N,N'-DI(DIHYDROXY-PROPYL) PIPERAZINE

Fine colorless crystals—melting point 127°–128° C.

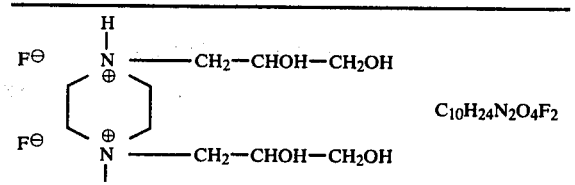

| Percentage composition | Calculated | Mol. wt. = 274 Found |
|---|---|---|
| Carbon % | 43.84 | 43.72 |
| Hydrogen % | 8.83 | 8,86 |
| Nitrogen % | 10.22 | 10.15 |

-continued $$F^{\ominus} \quad \underset{H}{\overset{H}{\underset{|}{N}}}\overset{\oplus}{\underset{\underset{|}{N}}{\bigcirc}}\overset{\oplus}{\underset{H}{\underset{|}{N}}}\text{—CH}_2\text{—CHOH—CH}_2\text{OH}$$

$$F^{\ominus}$$

C₁₀H₂₄N₂O₄F₂

Mol. wt. = 274

| Percentage composition | Calculated | Found |
|---|---|---|
| Fluorine % | 13.87 | 13.75 |

The test by NMR spectrometry shows that fluorohydrate has been formed.

The preparation of the tetrafluorohydrates of the above named bases occurs by dissolution at elevated temperature of a certain quantity of the chosen base in an excess of fluorohydric acid in aqueous solution of 40% or of 50%. Concentrate in the open with an I.R. lamp until dry and recrystallize in ethanol.

One obtains fine colorless crystals.

TETRAFLUOROHYDRATE OF N,N'-DI(HYDROXY-ETHYL) PIPERAZINE

Fine colorless crystals—melting point 66°–67° C.

$$F^{\ominus} \quad \underset{H}{\overset{H}{\underset{|}{N}}}\overset{\oplus}{\bigcirc}\overset{\oplus}{\underset{\underset{|}{N}}{}}\text{—CH}_2\text{—CH}_2\text{OH, HF}$$

C₈H₂₂N₂O₂F₄

Mol. wt. = 254

| Percentage composition | Calculated | Found |
|---|---|---|
| Carbon % | 37.83 | 31.1–37.63 |
| Hydrogen % | 8.73 | 8.42–8.40 |
| Nitrogen % | 11.03 | 11.40–10.89 |
| Fluorine % | 29.92 | 29.85–29.80 |

TETRAFLUOROHYDRATE OF N,N'-DI(DIHYDROXY-PROPYL) PIPERAZINE

Fine colorless crystals—melting point about 240° C. with decomposition.

$$F^{\ominus} \quad \underset{H}{\overset{H}{\underset{|}{N}}}\overset{\oplus}{\bigcirc}\overset{\oplus}{\underset{\underset{|}{N}}{}}\text{—CH}_2\text{—CHOH—CH}_2\text{OH, HF}$$

The chlorohydrates, bromohydrates and iodohydrates of said bases are prepared in the same manner. Examples of the products obtained are given below.

CHLOROHYDRATES
DI-CHLOROHYDRATES OF N,N'-DI-(BETA-HYDROXY-ETHYL) PIPERAZINE

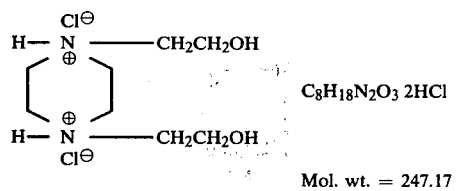

C₈H₁₈N₂O₃ 2HCl

Mol. wt. = 247.17

Fine colorless crystals - melting point 200° C. - soluble in water, in alcohols, glycols

| Percentage composition | Calculated | Found |
|---|---|---|
| C % | 38.86 | 38.82 |
| H % | 8.16 | 8.21 |
| Cl % | 28.69 | 28.69 |
| N % | 11.37 | 11.67 |

DI-CHLOROHYDRATE OF N,N'-DI-(BETA-GAMMA-DIHYDROXY-PROPYL) PIPERAZINE

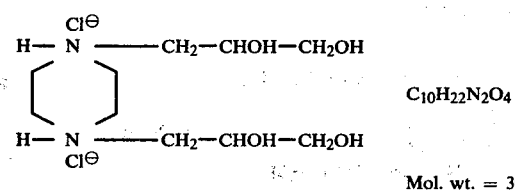

C₁₀H₂₂N₂O₄ 2HCl

Mol. wt. = 307.22

Fine colorless crystals - melting point 248°.

| Percentage composition | Calculated | Found |
|---|---|---|
| C % | 39.10 | 38.96–39.05 |
| H % | 7.87 | 7.65–7.70 |
| Cl % | 23.08 | 23.02–23.05 |

DI-CHLOROHYDRATE OF N,N'-DI-(BETA,GAMMA-EPOXY-PROPYL) PIPERAZINE

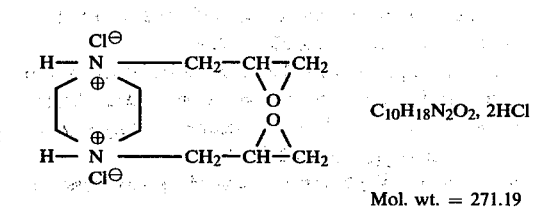

C₁₀H₁₈N₂O₂, 2HCl

Mol. wt. = 271.19

BROMOHYDRATES

DI-BROMOHYDRATE OF N,N'-DI-(BETA-HYDROXY-ETHYL) PIPERAZINE

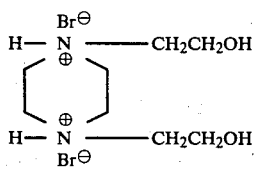 

$C_8H_{18}N_2O_2$, 2HBr

Mol. wt. = 336

Percentage composition

Colorless crystals - melting point 194° C. - soluble in water, in alcohols, the glycols

|     | Calculated | Found |
| --- | ---------- | ----- |
| C % | 28.59      | 28.52 |
| H % | 5.99       | 5.93  |
| Br % | 47.56     | 47.69 |

DI-BROMOHYDRATE OF N,N'-DI-(BETA,GAMMA-DIHYDROXY-PROPYL) PIPERAZINE

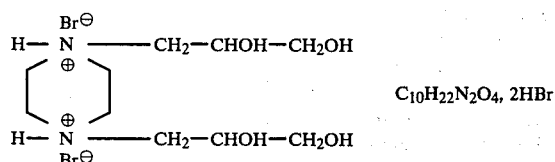 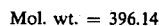

$C_{10}H_{22}N_2O_4$, 2HBr

Mol. wt. = 396.14

Percentage composition

Colorless pearly flakes - melting point 221°

|      | Calculated | Found |
| ---- | ---------- | ----- |
| C %  | 30.32      | 30.54 |
| H %  | 6.10       | 6.02  |
| Br % | 40.35      | 40.20 |
| N %  | 7.07       | 7.21  |

DI-BROMOHYDRATE OF N,N'-DI-(BETA,GAMMA-EPOXY-PROPYL) PIPERAZINE

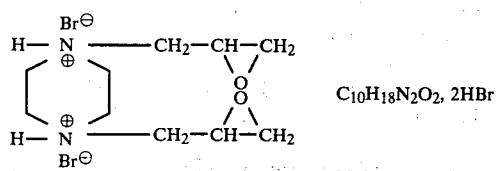 

$C_{10}H_{18}N_2O_2$, 2HBr

Mol. wt. = 360

IODOHYDRATES

DI-IODOHYDRATE OF N,N'-DI-(BETA-HYDROXY-ETHYL) PIPERAZINE

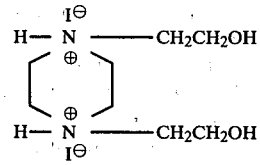 

$C_8H_{18}N_2O_2$, 2 IH

Mol. wt. = 430.076

Percentage composition

Fine light-yellow crystals - melting point 198° C. - soluble in water, in alcohols, the glycols

|     | Calculated | Found |
| --- | ---------- | ----- |
| C % | 23.33      | 22.24 |
| H % | 4.69       | 4.63  |
| I % | 59.04      | 59.02 |

DI-IODOHYDRATE OF N,N'-DI-(BETA,GAMMA-DIHYDROXY-PROPYL) PIPERAZINE

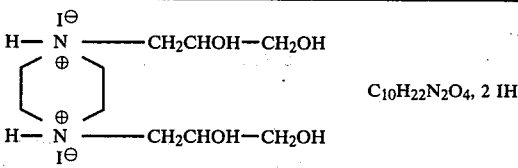 

$C_{10}H_{22}N_2O_4$, 2 IH

Mol. wt. = 490

Percentage composition

Fine colorless crystals - melting point 229°

|     | Calculated | Found |
| --- | ---------- | ----- |
| C % | 24.50      | 24.62 |
| H % | 4.94       | 5.06  |
| I % | 51.80      | 51.65 |

DI-IODOHYDRATE OF N,N'-DI-(BETA,GAMMA-EPOXY-PROPYL) PIPERAZINE

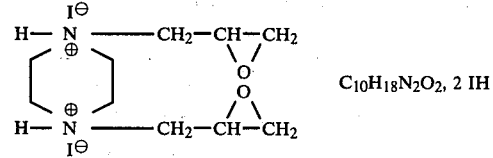 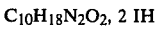

$C_{10}H_{18}N_2O_2$, 2 IH

Mol. wt. = 454

The toxicity studies of the halogeno-hydrates of the present invention have shown that at the doses used for their topical administration as anticariogenics their use presented no toxicity restriction.

By way of example there are described below the comparative tests made on difluorohydrate of N,N'-di(-hydroxyethyl) piperazine and on fluorohydrate of hexadecylamine or "ELMEX 242".

The acute toxicity was studies in rats and in mice.

The animals came from a homogeneous breed. The mice weighed between 19 and 21 g and the rats weighed from 120 to 140 g. The mice were grouped in lots of 10 and the rats in lots of 8. The animals underwent a one-week period of acclimatization in the animal house and were observed for 10 days after the drug administrations.

The administrations took place orally at a volume of 0.5 ml per 20 g of mouse and 1 ml per 100 g of rat. The $LD_{50}$ was determined by the method of Lichfield and Wilcoxon.

As regards the difluorohydrate of N,N'-di(hydroxyethyl) piperazine, the administered solution was prepared by diluting the mother solution to 65.4%, the dilutions being made after having weighed this solution. The administered dose is expressed by weight, taking account of the indicated strength of this solution.

For the solid "ELMEX 242" an aqueous suspension was prepared with the aid of solubilizing agents (e.g. Tween-polyoxyethylene sorbitan monolaurate). A very thick suspension is then obtained which tends to foam heavily, is difficult to get into the esophageal sound, and the determination of its volume is rendered difficult by the foam.

The results obtained with the "ELMEX" are therefore rather approximate.

The following tables indicate the results obtained.

1. ELMEX 242
Mouse - oral

| Doses (mg/kg) | 600 | 800 | 1000 | 1250 | 1500 | 1750 | 2000 | 2500 |
|---|---|---|---|---|---|---|---|---|
| Animals per lot | 10 | 10 | 10 | 10 | 10 | 10 | 10 | 10 |
| Deaths | | | | | | | | |
| D + 1 | 0 | 0 | 1 | 1 | 4 | 3 | 9 | 10 |
| D + 2 | 0 | 0 | 2 | 2 | 7 | 4 | 10 | 10 |
| D + 5 | 0 | 0 | 2 | 3 | 9 | 9 | 10 | 10 |
| D + 10 | 0 | 0 | 2 | 3 | 9 | 9 | 10 | 10 |
| $LD_{50}$ = 1250 mg/kg | | | | | | | | |

The animals have diarrhea. The mice are totally immobile and tremble. Death occurs in a few hours; for others recovery is also fairly rapid.

Rat - oral

| Doses (mg/kg) | 125 | 150 | 500 |
|---|---|---|---|
| Animals per lot | 8 | 8 | 8 |
| Deaths D + 10 | 0 | 0 | 0 |

The behavior of the animals is normal.

2. Difluorohydrate of N,N'-di(hydroxy-ethyl) piperazine
Mouse - oral

| Doses (mg/kg) | 200 | 300 | 400 | 500 | 600 | 700 | 800 | 1000 |
|---|---|---|---|---|---|---|---|---|
| Animals per lot | 10 | 10 | 10 | 10 | 10 | 10 | 10 | 10 |
| Deaths | | | | | | | | |
| D + 1 | 0 | 0 | 2 | 3 | 4 | 9 | 7 | 10 |
| D + 2 | 0 | 0 | 3 | 5 | 7 | 10 | 8 | 10 |
| D + 5 | 0 | 0 | 3 | 5 | 8 | 10 | 9 | 10 |
| D + 10 | 0 | 0 | 3 | 5 | 8 | 10 | 9 | 10 |
| $LD_{\%0}$ = 475 mg/kg | | | | | | | | |

No symptom occurs up to the dose of 400 mg/kg. At higher doses the mice are totally immobile. They show light trembling, but over the entire body, also diarrhea. Coma sets in in about 45 minutes. Death occurs after one hour at the highest doses. The ill state generally persists for at least 24 hours and then improves slowly.

Rat - oral

| Doses (mg/kg) | 250 | 500 | 750 | 1000 | 1250 |
|---|---|---|---|---|---|
| Animals per lot | 8 | 8 | 8 | 8 | 8 |
| Deaths D + 1 | 0 | 0 | 1 | 2 | 5 |
| D + 2 | 0 | 0 | 3 | 5 | 7 |
| D + 5 | 0 | 0 | 4 | 6 | 8 |
| D + 10 | 0 | 0 | 4 | 6 | 8 |
| $LD_{50}$ = 790 mg/kg | | | | | |

The symptomatology is not very clear. Some diarrhea and some trembling appear.

In conclusion, to the extent that one can compare a solution with a suspension, the product according to the invention appears clearly more toxic than "ELMEX 242". However, it should be noted that in the rat we were limited to the dose of 500 mg/kg of "ELMEX" because of the thickness of the suspension.

The fluorohydrates according to the invention possess very remarkable anticariogenic properties, because of the presence of a large proportion of ionizable fluoride in the organic molecule. For example, the difluorohydrate of N,H'-di(hydroxy-ethyl) piperazine contains 15.18% ionizable fluorine.

It is known that topical fluorine has a cariostatic action by direct contact with the tooth and the buccal medium. The fluorine acts on the tooth by strengthening its mineral structure for formation of fluoro-apatite and by favoring the crystallinity of the calcium phosphates and their precipitation in the stable form of hydroxyapatite. In the enamel this action is reflected in a greater resistance to outside agents and reduced solutility in the cariogenic acids.

On the buccal medium of the saliva and of the dental plaque topical fluorine has an anti-enzymatic and bacteriostatic action which slows or inhibits the aggressivity of the cariogenic acids. This action is accompanied by an anti-inflammatory action.

Topical fluorine also has the effect of reducing the phenomena of dental hypersensitivity.

The anticariogenic activity of the difluorohydrate of N,N'-di(hydroxy-ethyl) piperazine has been evidenced by comparison with sodium fluoride known for its carioppreventive topical properties. A comparative study has been made of the penetration into the dental enamel of the fluorine contained in the molecule according to the invention and of the fluorine contained in sodium fluoride.

For this comparison the difluorohydrate of N,N'-di(-hydroxy-ethyl) piperazine was marked at the fluorine 18, by isotopic exchange by dissolving some crystals of the product according to the invention in a solution of pure fluorine 18 without entrainer. The same was done for the sodium fluoride.

The study of the penetration of the fluorine into the enamel was made on several teeth to compare the behavior of the product of the invention and of sodium fluoride in supplying fluorine and in the penetration of the latter into the deepest layers of the dental tissue.

The tests were performed on 30 premolar teeth taken from normal children 9 to 11 years old. Eighteen teeth were treated by topical application of the radioactive solutions of the difluoro-hydrate of N,N'-di(hydroxy-ethyl) piperazine or of NaF adjusted to pH=3.5; the other 12 were treated with the same solutions adjusted to a pH of 7.4.

The radioactive solutions are obtained by dissolving 69 mg of the difluorohydrate and 81.3 mg of NaF, respectively, in 1 and 3 ml of fluorine 18 solution without entrainer. Thus solutions titering 1.23% fluorine are obtained.

Acid solutions

As the difluorohydrate solution is already at pH=3.5, it is sufficient to acidify the NaF solution by addition of about 0.2 ml hydrochloric acid 6 M, to 3 ml of the radioactive solution.

Neutral solutions

In this case, the difluorohydrate's nature of organic salt can be preserved and its solution neutralized at 1.23% of fluorine in 1 ml by addition of about 110 mg of its N,N'-di(hydroxyethyl) piperazine base.

The radioactivity of the solutions thus obtained is about 1 m Ci/mM.

The acidification of neutralization of these solutions brings in an element of imprecision in the quantitative analysis by radioactive tracer because it changes the fluorine titer of the solutions, as the difluorohydrate solution always involves an error in its titer due to the weighing of this particularly hygroscopic compound.

For the experimentation one determines two enamel plagues on each tooth. For this, one applies on the crowns, separated from each other by 2 or 3 mm, two round disks of a diameter of 3 mm cut out from adhesive tape. The crown is then covered with a layer of impermeable varnish. When the varnish is dry, the patches of adhesive tape are removed, thus bearing the two zones of enamel to be treated.

For the electrolytic application, one introduces through the apex of the tooth a platinum wire (diameter 0.2 mm), which is connected to the anode.

The electrolytic application of the solutions is done by means of an apparatus such as a galvanoster, which supplies a d-c voltage of 9 volts.

The spot application of the fluorinated solution is done by means of a sponge imbibed with 0.5 ml of the solution. This sponge is inserted in a polyethylene tube to limit the surface of contact between tooth and sponge to the circumference of the enamel zone treated.

The sampling of the enamel is done by Muhlemann's biopsy technique: A patch of blotting paper impregnated with 4 microliters of perchloric acid 2 M is applied on the trated enamel for 30 seconds. The enamel is dried with a second patch of blotting paper. It is on these patches which contain the dissolved enamel that we measure the radioactivity.

For the results obtained by this technique to be valid, the fluorine determined must have only one possible origin—that of the applied treatment. There has been ascertained, therefore:

(a) The proper protection of the enamel by the varnish:

A tooth provided with its two disks of adhesive tape has been varnished, and it has been subjected to a topical application of 10 minutes. Then the tooth was raised with distilled water for 30 seconds, and the absorbed fluorine was counted:

| Tooth: | 340 c/min |
|---|---|
| Backround noise: | 175 c/min |
| Sampling on a treated tooth: | 3000 c/min |

The fluorine did not pass through the varnish, which therefore assures adequate protection.

(b) Little absorption of fluorine by the varnish:

The window cut in the varnish keeps "burrs" of varnish around it. It was important to know if these "burrs" retained much fluorine.

A polyethylene tube (which does not absorb fluorine) was covered with a layer of varnish in which an opening was made. This opening was subjected to a topical application of 10 minutes and to a rinsing with distilled water. The fluorine absorbed was then counted.

| Polyethylene tube: | 300 c/min |
|---|---|
| Backround noise: | 185 c/min |
| Sampling on a treated tooth: | 5000 c/min |

The quantity of fluorine absorbed is therefore negligible and there is no risk of its falsifying the results.

(c) Non-interference topical zone—electrolytic zone:

Teeth were treated topically or electrolytically by fluorinating only one area while keeping the second as reference to show possible internal migration of the fluorine.

After fluorination and rinsing with water, a biopsy was taken of the two areas and the radioactivity of the fluorine measured.

In both the electrolytic and topical tests, presence of fluorine was not discovered in the reference zone (cf. Table I).

(d) Constancy of the enamel sampling:

It is important to dissolve an identical quantity of enamel on each of the zones treated, for an obvious reason: The quantity of fluorine measured increases with the thickness of enamel sampled.

Muhlemann consideres that by applying the same acid solution for the same period of time on different teeth, he dissolves the same thickness of enamel.

RESULTS

There are given in Table I all the results relating to the acid treatment, in Table II all the results relating to the treatment at neutral pH. The fluorine values are those obtained by measuring the radioactivity of the samples.

The columns $G_1$ and $N_2$ represent the mass of fluorine measured on the second biopsy.

We have marked $R_1$ and $R_1$ and $R_2$ the ratios $G_1/G_2$ and $N_1/N_2$, and $R_3$ the ratio.

$$\frac{G_1 + G_2}{N_1 + N_2}$$

$R_1$ and $R_2$ permitting to compare the quantities of fluorine at the same depth. $R_3$ permits comparing the accumulation of fluorine in the tooth.

Treatment in acid medium

The ratio $R_1$ is less than 1 in 16 out of 18 cases.

The fluorine, therefore, is more abundant in the second biopsy. The reason for this is a greater sampling of enamel which is less resistant in depth; it does not mean that the fluorine concentration of the enamel is greater in depth.

The ratio $R_2$ is less than 1 to 7 out of 18 cases, and greater in 6 cases. The values of $R_1$ scatter widely, which may be the result of an irregular sampling of enamel.

The ratio $R_3$ is less than 1 in 5 out of 18 cases, between 1 and 1.7 in 8 cases, and greater than 1.7 in 4 cases. It ranges about a mean value of 1.5 with a standard deviation of 0.6.

Treatment in neutral medium $R_1$ is greater than 1 in 10 out of 12 cases and $R_2$ in all out of 12 cases. Their mean value is respectively 3.0 and 3.6, which shows that the penetration of the fluorine in depth is much less great than in the case of treatment in acid medium.

The ratio $R_3$ is less than 1 in 3 out of 12 cases, between 1 and 1.7 in 7 cases, and greater than 1.7 in 2 cases. Here, too, the results scatter widely and range about an average of 1.2 with a standard deviation of 0.4.

Comparison of the two treatments

If we compare the average of the fluorine sampled in the two biopsies made in the treatment at acid pH with the average of the fluorine sampled in the two biopsies made in the treatment at neutral pH, we obtain:
2.6 in the case of GD 12
3.6 in the case of NaF
which shows that the acidification of the solutions very definitely favors the penetration of the fluorine into the enamel.

The wide scatter of the results does not enable us to infer the superiority of one or the other of the fluorinated molecules. It seems that their behavior in acid medium and in neutral medium is the same.

It is seen that the influence of the pH is determining and modifies in considerable proportions the penetration of the fluorine into the enamel.

An acid pH favors the penetration of the fluorine into the enamel in greater quantity and in greater depth.

TABLE I

Topical application of GD 12 ($G_1$ and $G_2$) and of NaF ($N_1$ and $N_2$) at pH 3.5

| Teeth | G1 | G2 | R1 | N1 | N2 | R2 | R3 |
|---|---|---|---|---|---|---|---|
| 1 | 950 | 1250 | 0.76 | 1030 | 360 | 2.86 | 1.58 |
| 2 | 360 | 1420 | 0.25 | 2500 | 410 | 6.09 | 0.61 |
| 3 | 430 | 640 | 0.67 | 280 | 410 | 0.68 | 1.55 |
| 4 | 320 | 510 | 0.63 | 290 | 500 | 0.58 | 1.06 |
| 5 | 870 | 1400 | 0.62 | 480 | 400 | 1.20 | 2.58 |
| 6 | 540 | 970 | 0.56 | 1800 | 3080 | 0.58 | 0.31 |
| 7 | 410 | 600 | 0.68 | 360 | 380 | 0.94 | 1.36 |
| 8 | 530 | 730 | 0.73 | 760 | 1711 | 0.44 | 0.51 |
| 9 | 331 | 245 | 1.35 | 221 | 74 | 2.99 | 1.96 |
| 10 | 909 | 943 | 0.96 | 856 | 553 | 1.53 | 1.31 |
| 11 | 240 | 354 | 0.68 | 224 | 240 | 0.93 | 1.28 |
| 12 | 311 | 430 | 0.66 | 472 | 1070 | 0.44 | 0.48 |
| 13 | 190 | 156 | 1.21 | 130 | 47 | 2.76 | 1.95 |
| 14 | 532 | 552 | 0.99 | 535 | 346 | 1.54 | 1.22 |
| 15 | 300 | 310 | 0.97 | 430 | 170 | 2.53 | 1.01 |
| 16 | 316 | 550 | 0.57 | 180 | 170 | 1.05 | 2.47 |
| 17 | 305 | 340 | 0.90 | 533 | 290 | 1.83 | 0.90 |
| 18 | 280 | 340 | 0.82 | 429 | 120 | 3.57 | 1.13 |

TABLE II

Topical application of GD 12 ($G_1$ and $G_2$) and of NaF ($N_1$ and $N_2$) at pH 7.4

| Teeth | G1 | G2 | R1 | N1 | N2 | R2 | R3 |
|---|---|---|---|---|---|---|---|
| 1 | 102 | 38 | 2.68 | 177 | 75 | 2.36 | 0.55 |
| 2 | 75 | 23 | 3.26 | 87 | 11 | 7.91 | 1.00 |
| 3 | 421 | 37 | 11.37 | 163 | 58 | 2.81 | 2.07 |
| 4 | 912 | 240 | 3.80 | 775 | 141 | 5.50 | 1.25 |
| 5 | 290 | 76 | 3.81 | 160 | 17 | 9.41 | 1.50 |
| 6 | 207 | 128 | 1.62 | 217 | 65 | 3.34 | 1.18 |

TABLE II-continued

Topical application of GD 12 ($G_1$ and $G_2$) and of NaF ($N_1$ and $N_2$) at pH 7.4

| Teeth | G1 | G2 | R1 | N1 | N2 | R2 | R3 |
|---|---|---|---|---|---|---|---|
| 7 | 139 | 98 | 1.42 | 205 | 97 | 2.11 | 0.78 |
| 8 | 191 | 62 | 3.08 | 140 | 79 | 1.77 | 1.15 |
| 9 | 288 | 100 | 2.88 | 194 | 126 | 1.54 | 1.21 |
| 10 | 208 | 193 | 1.08 | 247 | 73 | 3.38 | 1.25 |
| 11 | 127 | 179 | 0.71 | 293 | 98 | 2.98 | 0.78 |
| 12 | 394 | 506 | 0.78 | 190 | 330 | 0.52 | 1.73 |

We thus conclude that with respect to its anticariogenic action the difluorohydrate of N,H'-di(hydroxyethyl) piperazine has effects comparable to those of sodium fluoride, under the same pH conditions, to which effects are added its other bacteriostatic and bactericidal activities. These properties destine this product to a use in dentistry in the form of solutions, mouth washes, varnish gels, obturation materials, dentrifices.

The fluorine concentration of these different preparations may be comprised between 100 mg and 2 g percent, that is, expressed, in difluorohydrate of N,N'-di(hydroxy-ethyl) piperazine, between 660 mg and 13 g of the latter per 100 g of finished product.

The preferred polyhydroxyalkyl compounds for use in the present invention are those having up to 5 carbon atoms.

Such preparations are particularly efficient in the prevention and treatment of dental decay, of inflammatory diseases of the periodontium and of dentinal hyperesthesia.

What is claimed is:

1. An orally administrable pharmaceutical dosage form comprising from about 0.66 to 13% by weight of a compound of the formula

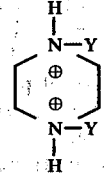

wherein Y is a member selected from the group consisting of hydroxyalkyl, dihydroxyalkyl and epoxyalkyl wherein alkyl is $C_2$–$C_4$ and from about 87 to about 99.66% by weight of a carrier material.

2. A method for preventing dental caries in a human which comprises orally administering to said human the pharmaceutical dosage form of claim 1.

3. A pharmaceutical composition as defined in claim 1 wherein said carrier is selected from the group consisting of a liquid carrier and a solid carrier.

4. A pharmaceutical composition as defined in claim 3 wherein said liquid carrier is water.

5. A pharmaceutical composition according to claim 4 wherein the compound is N,N'-di(hydroxy-ethyl) piperazine di-fluorohydrate.

6. A compound of the formula

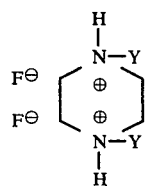

where Y is a member selected from the group consisting of hydroxyalkyl, dihydroxyalkyl and epoxyalkyl wherein alkyl is $C_2$–$C_4$.

7. N,N'-di(hydroxyl-ethyl) piperazine di-fluorohydrate of the formula

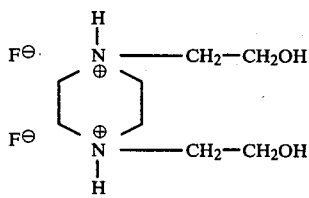

8. N,N'-di(hydroxy-propyl) piperazine di-fluorohydrate of the formula

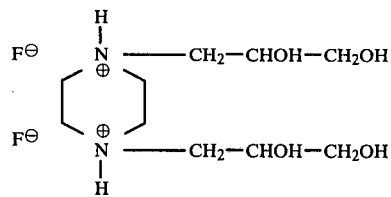

9. N,N'-di(epoxy-propyl) piperazine di-fluorohydrate of the formula

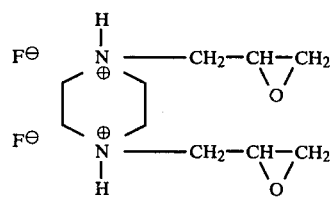

10. N,N'-di(hydroxy-propyl) piperazine tetra-fluorohydrate of the formula

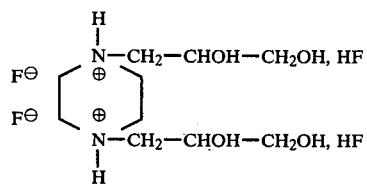

11. N,N'-di(hydroxy-ethyl) piperazine tetrafluorohydrate of the formula

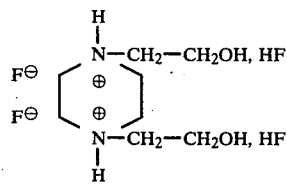

* * * * *